(12) United States Patent
San et al.

(10) Patent No.: US 8,207,313 B2
(45) Date of Patent: Jun. 26, 2012

(54) NATURAL PRODUCTS FROM VINCA

(75) Inventors: Ka-Yiu San, Houston, TX (US); Ill-Min Chung, Seoul (KR); Ateeque Ahmad, Lucknow (IN)

(73) Assignee: William Marsh Rice University, Houston, TX (US)

( * ) Notice: Subject to any disclaimer, the term of this patent is extended or adjusted under 35 U.S.C. 154(b) by 364 days.

(21) Appl. No.: 12/527,689

(22) PCT Filed: Feb. 18, 2008

(86) PCT No.: PCT/US2008/054225
§ 371 (c)(1),
(2), (4) Date: Oct. 14, 2009

(87) PCT Pub. No.: WO2008/101238
PCT Pub. Date: Aug. 21, 2008

(65) Prior Publication Data
US 2010/0048494 A1  Feb. 25, 2010

Related U.S. Application Data

(60) Provisional application No. 60/977,647, filed on Oct. 4, 2007, provisional application No. 60/890,482, filed on Feb. 18, 2007.

(51) Int. Cl.
*C07H 15/00* (2006.01)
*C07H 17/00* (2006.01)
*C07G 3/00* (2006.01)
*C07G 11/00* (2006.01)
*A01N 43/04* (2006.01)
*A61K 31/70* (2006.01)

(52) U.S. Cl. ............ 536/8; 536/4.1; 514/25; 514/27; 514/28

(58) Field of Classification Search ............ 536/8, 4.1; 514/25, 27, 28
See application file for complete search history.

(56) References Cited

U.S. PATENT DOCUMENTS

| 4,066,507 | A | 1/1978 | Takagi et al. |
| 4,753,929 | A | 6/1988 | Matsumoto et al. |
| 5,750,709 | A | 5/1998 | Castor |
| 6,555,523 | B1 | 4/2003 | Prendergast |

OTHER PUBLICATIONS

Scott, I.M., Martin, G.C., Horgan, R., Heald, J.K. (1982) Mass spectrometric measurement of zeatin glycoside levels in *Vinca rosea* L. crown gall tissue. Planta, vol. 154, p. 273-276.*
Li, Y.-M., Zhao, Y.-Y., Fan, Y.-B., Wang, X., Cai, L-N. (1997) Flavonoids from *Speranskia tuberculata*. Journal of Chinese Pharmaceutical Sciences, vol. 6, No. 2, p. 70-74.*
Kadota, S., Basnet, p., Hase, K., Namba, T. (1994) Matteuorienate A and B, Two New and Potent Aldose Reductase Inhibitors from *Matteuccia orientalis* (Hook.) Trev. Chemical and Pharmaceutical Bulletin, vol. 42, No. 8, p. 1712-1714.*
PCT/US08/54225 Search Report, Aug. 19, 2008, Rice University.
Ahmad and Chung. A New Aliphatic Glycoside Constituent from the Hairy Root Cultures of *C. roseus*. Asian Journal of Chemistry. 20: 642-8 (2008).
Bhadra, et al., "Production of indole alkaloids by hairy root lines of *C. roseus*." Biotechnol. Bioeng., 41:581-92 (1993).
Chung, et al., "A new chemical constituent from the hairy root cultures of *C. roseus*." Bull. Korean Chem. Soc. 28:229-34 (2007).
Chung, et al.,. Identification of new compounds from *C. roseus* hairy root cultures. Bull. Korean Chem. Soc. 28: 1294-8 (2007).
Chung, et al., "New Sesquiterepene Glycosides from Cultures Hairy Roots of *C. roseus*." Chin. J. Chem.. 25: 1695-99 (2007).
Chung, et al., "New *Catharanthusopirnaranoside* A and B from Culture Hairy Roots of *C. roseus*." Chemistry of Natural Compounds (2008a) [Accepted].
Chung, I.L., et al., Flavonoid Glucosides From the Hairy Roots of *Catharanthus roseus*. J. Nat. Prod. 72; 613-620 (2009).
Brun et al., A new flavonol glycoside from *Catharanthus roseus*. Phytochemistry 50:167-9 (1999).
Kitajima, et al., "Two new triterpenoid sulfates from the leaves of *Schefflera octophylla*." Chem. Pharm. Bull. 38:714-6 (1990).
Knobloch, et al., "Medium and light induced formation of serpentine and anthocyanins in cell suspension cultures of *C. roseus*." Phytochemistry 21:591-4 (1982).
Luijendijk, et al., Involvement of Strictosidine as a defensive chemical in *C. roseus*. J. Chemical Ecology 22:1355-66 (1996).
Moreno, et al., "Effects of elicitation on different metabolic pathways in *C. roseus* (L.)G.Don cell suspension cultures." Enzyme and Microbial Technology, 18:99-107 (1996).
Moreno, et al., "Cell and tissue cultures of *C. roseus* (L.) G. Don: A literature survey II. Updating from 1988 to 1993". Plant Cell Tiss. Org. Cult 42:1-25 (1995).
Seitz, et al., "Elicitor-mediated induction of phenylalanine ammonia lyase and tryptophan decarboxylase: Accumulation of phenols and indole alkaloids in cell suspension cultures of *C. roseus*." Plant Cell Tiss. Org Cult. 18:71-8 (1989).
Daniel, M., et al., Chemotaxnomical Studies on *Apocynaceae*. Indian J. Exp. Bol., vol. 16 (1978).

* cited by examiner

*Primary Examiner* — Scarlett Goon
(74) *Attorney, Agent, or Firm* — Boulware & Valoir

(57) ABSTRACT

New and useful compounds *C. roseus* cultured hairy roots are provided, by Isolating flavone glycosides together with a pharmaceutically acceptable carrier. This is accomplished by immersing powdered the hairy roots in methanol to produce an extract, concentrating the extract, resuspending the extract in water, extracting the compound with organic solvent, and isolating the compound from the organic solvent.

8 Claims, 2 Drawing Sheets

NATURAL PRODUCTS FROM VINCA

CROSS-REFERENCE TO RELATED APPLICATIONS

This application is a 35 U.S.C. Section 371 of PCT/US2008/054225 filed Feb. 18, 2008, which claims priority to U.S. Provisional Application Ser. No. 60/890,482 filed Feb. 18, 2007 entitled "Natural Products from *Vinca*," and Ser. No. 60/977,647 filed Oct. 4, 2007 entitled "Flavonoid Glycosides from *Catharanthus Roseus* Hairy Roots," which are incorporated herein by reference in their entirety.

FEDERALLY SPONSORED RESEARCH STATEMENT

Not applicable.

REFERENCE TO MICROFICHE APPENDIX

Not applicable.

FIELD OF THE INVENTION

The invention relates to compounds isolated from *Catharanthus roseus* hairy root cultures, and their use for the treatment of inflammatory conditions.

BACKGROUND OF THE INVENTION

The periwinkle, *Catharanthus roseus* (L.) G. Don, also known as *Apocynaceae, Vinca rosea* L and *Herba Catharanthi*, is widely used an ornamental and medicinal plant. *C. roseus* is a herbaceous shrub and has been extensively studied because the leukemia drugs vincristine and vinblastine were originally obtained from this herb. Many other useful drugs have since been isolated from this plant or its cell cultures.

This research has identified twelve new and useful compounds from *C. roseus* cultured hairy roots, four of which have already been shown to have activity against MMP-9 and TNF-α, suggesting their use as anti-inflammatory medicaments. Testing is ongoing against the remaining compounds, and it is expected that they will show similar pharmaceutical activities.

SUMMARY OF THE INVENTION

TABLE 1

Abbreviations.

| Abbr. | Description |
|---|---|
| COSY | Correlation Spectroscopy |
| DEPT | Distortionless Enhancement by Polarisation Transfer |
| EI/MS | Electron Ionization/Mass Spectroscopy |
| ELISA | Enzyme Linked Immunosorbent Assay |
| FAB/MS | Fast Atom Bombardment/Mass Spectroscopy |
| FT-IR | Fourier Transform-Infrared |
| HETCOR | Heteronuclear Correlation Spectroscopy |
| HMBC | Heteronuclear Multiple-Bond Correlation |
| HPLC | High Performance Liquid Chromatography |
| HR-FAB/MS | High-Resolution FAB/MS |
| HSQC | Heteronuclear Single Quantum Correlation |
| IR | Infrared |
| LPS | Lipopolysaccharide |
| MMP | Matrix Metalloproteinase |
| MMP-2 | Matrix metalloproteinase 2 |
| MMP-9 | Matrix metalloproteinase 9 |
| MTS | 3-(4,5-dimethylthiazol-2-yl)-5-(3-carboxymethoxyphenyl)-2-(4-sulfophenyl)-2H-tetrazolium |
| NMR | Nuclear Magnetic Resonance |
| ODS | Octadecylsilane |
| THP-1 | Human acute monocytic leukemia cell line |
| TLC | Thin Layer Chromatography |
| TNF-α | Tumor Necrosis Factor-alpha |
| TMS | tetramethylsilane |

As used herein, "isolated" means removed from its natural plant environment. In one embodiment, "isolated" means compounds isolated through column chromatography after extraction from naturally cultured *C. roseus* hairy roots.

As used herein, "purified" means at least or greater than 75% purity, and preferably at least or greater than 80, 85, or 90% purity. Purity levels as high as 95, 96, 97, 98% have been achieved herein, and 99 and 100% purity may be possible. Purity is measured by HPLC.

As used herein, "organic solvent" is a carbon-containing chemical solvent. Some examples of organic solvents include tetrachloroethylene, toluene, acetone, methyl acetate, ethyl acetate, hexane, ethanol, methanol, butanol, dichloromethane, chloroform, as well as other organic solvents. In one embodiment, ethyl acetate and butanol are used to isolate compounds. In another embodiment ethyl acetate and methanol are used to extract compounds. A skilled artisan can select organic solvents based on chemical properties to achieve desired properties under a variety of conditions.

When the purity of a compound used to formulate a pharmaceutical composition is discussed herein, we refer to the purity of the compound before admixture with pharmaceutical carriers and/or other excipients. Thus, a composition might be made with 95% pure compound, but be only 50% pure in the final composition if significant carrier and excipients are added thereto.

The present invention is related to isolation and identification of new natural compounds from *C. roseus* and related or similar species. In a preferred embodiment, the compounds is isolated cultured hairy roots, and preferably from a methanol extract of *C. roseus* cultured hairy roots.

The novel compounds include:

TABLE 2

Compounds Isolated from *C. roseus* hairy root culture methanol extract.

| Compound | Structure |
|---|---|
| (1) 3,5,7-trihydroxy-3',4'-dimethoxy-flavone-7β-D-gluco-pyranosyl (4"-13''') 2''',6''',10''',14'''-tetramethyl hexadec-14-ene | |
| (2) 3,5,7-trihydroxy-4'-methoxy-flavone-3β-D-gluco-pyranosyl (4"-13''')-2''',6''',10''',14'''-tetramethyl hexadecane. | |
| (3) 6"-(3''',11'''-dimethyl dodec-3''',7'''(14'''),10'''-trienyl gluco-pyranosyl-7-hydroxy-3',4'-dimethoxy-flavanone | |
| (4) 6"-(3''',11'''-dimethyl-7'''-hydroxy-methylene dodecanyl) gluco-pyranosyl-7,3'-dihydroxy-4'-methoxy-flavanone. | |

TABLE 2-continued

Compounds Isolated from *C. roseus* hairy root culture methanol extract.

| Compound | Structure |
|---|---|
| (5): n-heptacosan-13α-ol-13β-D-glucopyranoside | 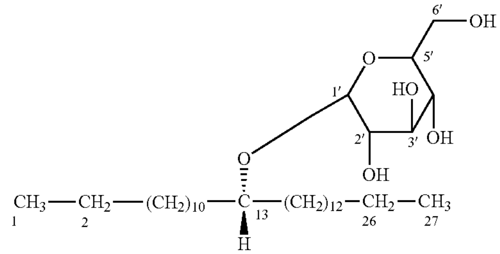 |
| (6) 3,7,11,19,23,27-hexamethyl-15-hydroxymethylene-n-octacos-5,8,20-triene-10β,18α-diol-10β-D-glucopyranoside | 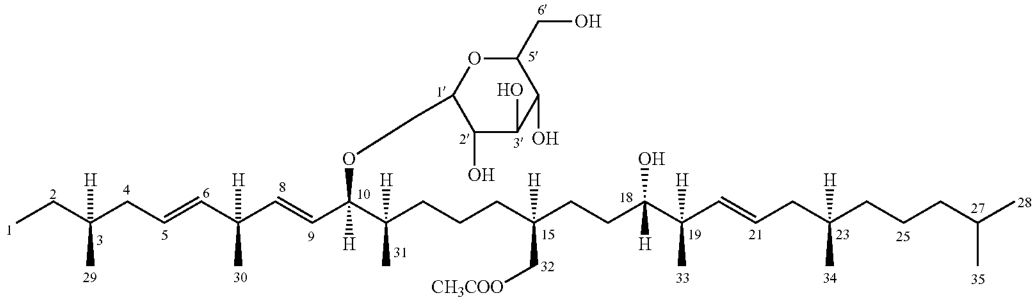 |
| (7). Lanast-5,8-dien-3β-ol-27-oic acid-3β-D-glucopyranosyl (4'-1''-dimethoxy anthracene | 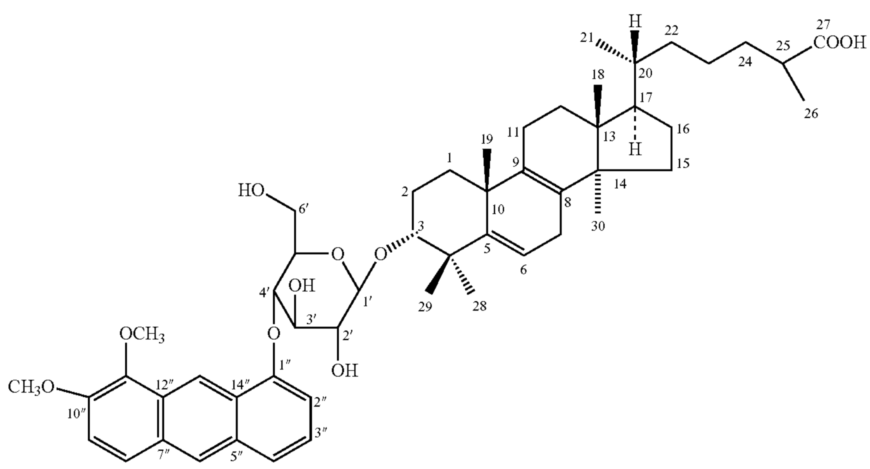 |
| (8) 2-methoxy-6-(n-nonacontan-5'',6''-dionyl)-11-hydroxy-13-methyl-11β-D-rhamnopyranoside anthracene | 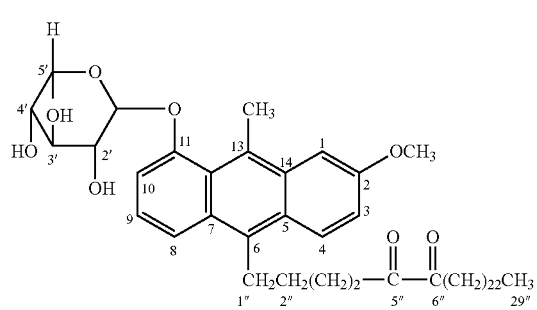 |

TABLE 2-continued
Compounds Isolated from *C. roseus* hairy root culture methanol extract.
| Compound | Structure |
|---|---|
| (9) 3-methoxy-6,8-dimethyl-β-naphthyl-β-D-gluco-puranosyl-6'-pimaran-17''-oic acid ester. | 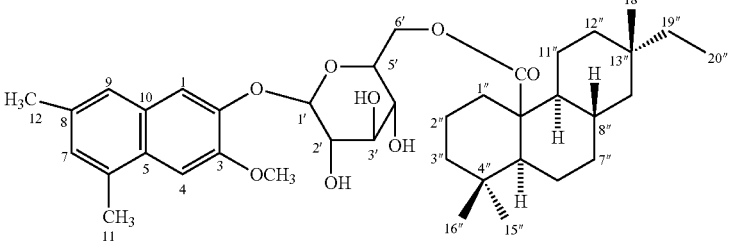 |
| (10) 1-methoxy-7,8-dimethyl-β-naphthyl-β-D-gluco-puranosyl-4'-pimaran-17''-oic acid ester. | 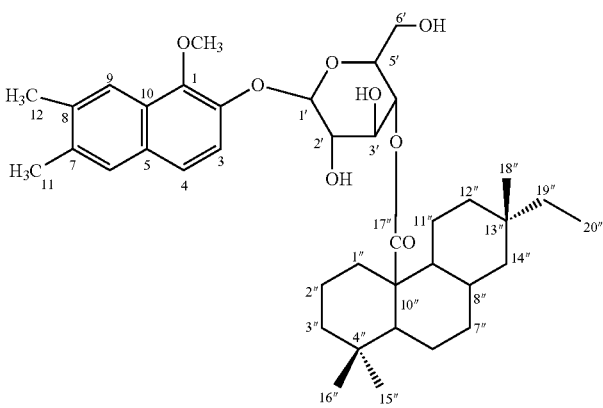 |
| (11) guaia-1,7-dien-3β,13-diol-13α-D-gluco-furanoside | 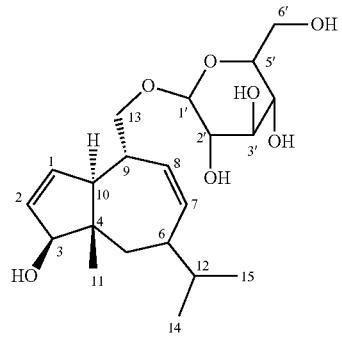 |
| (12) cadin-2-en-1β-ol-1β-D-glucurono-pyranoside | 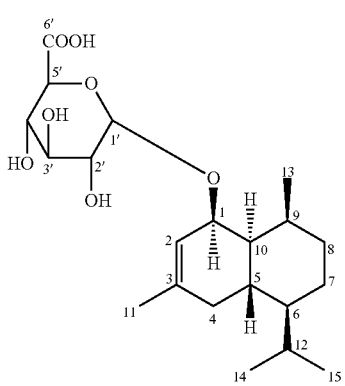 |

TABLE 2-continued

Compounds Isolated from *C. roseus* hairy root culture methanol extract.

| Compound | Structure |
|---|---|
| (13) 3-epibetulinic acid -known- | [pentacyclic triterpene structure with 3α-OH, 17-COOH, and 29-exomethylene; numbered positions 1–30] |
| (14) n-pentadecanyl octa-dec-19-en-oate -known- | $CH_3-(CH_2)_7-CH=CH-(CH_2)_7-C(=O)-O-CH_2-(CH_2)_{12}-CH_3$ (positions 18, 10, 9; 1′, 15′) |
| (15) n-hentetracont-36-en-5β-ol -known- | $CH_3(CH_2)_3CH=CH-(CH_2)_{30}-CH(OH)-(CH_2)_3-CH_3$ (positions 41, 37, 36, 5, 1) |
| (16) β-sitosterol -known- | [sterol structure with 3β-OH, Δ5 double bond, 24-ethyl side chain; numbered positions 1–29] |

The invention also provides the first reported isolation of pharmaceutical compounds from *C. roseus* hairy root cultures. Hairy root cultures are a preferred source material as they are easy to grow in large quantities under controlled conditions.

BRIEF DESCRIPTION OF THE DRAWINGS

FIGS. 1A, C, E, and G shows expression of MMP-9 in response to compounds 1-4, and using MMP-2 as an internal control. Fig. B, D, F, and H shows cell viability with the same 4 compounds.

DESCRIPTION OF EMBODIMENTS OF THE INVENTION

Figure 1:
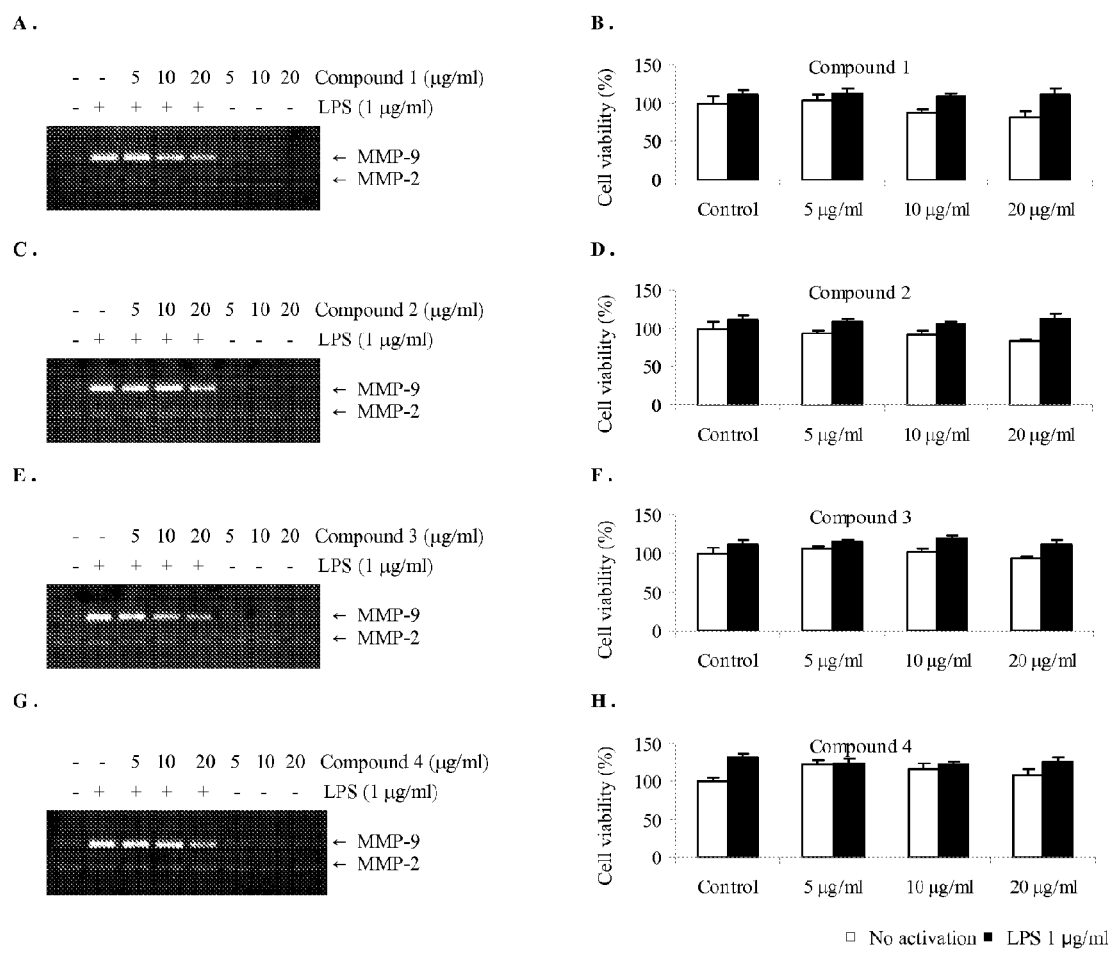
FIG. 1 shows compounds (1), (2), (3), and (4) were tested for inhibition of MMP9 and cell growth with and without stimulation of inflammation by LPS. Each compound inhibits MMP-9 expression in a dose dependant manner, but has no negative impact on cell viability, suggesting its use as a medicament to treat MMP-9 mediated conditions such as inflammation.

Chemicals. All chemicals were of an analytical grade: hexane, ethyl acetate, methanol, ethanol, sulphuric acid and vanillin were purchased from DAEJUNG CHEMICALS AND METALS™ (Seoul, South Korea). Pre-coated TLC plates (layer thickness 0.5 mm), silica gel for column chromatography (70-230 mesh ASTM) and LiChroprep® RP-18 (40-63 μm) were from MERCK® (Darmstadt, Germany). Authentic standards of β-sitosterol (16), oleic acid, and D-glucose were purchased from Sigma-Aldrich (St. Louis, Mo., USA).

Culture conditions: The hairy root line used in this study was previously generated by infection of *C. roseus* seedling with *Agrobacterium rhizogenes* 15834 (Bhadra, 1993 incorporated herein by reference in its entirety). The culture media consisted of a filter-sterilized solution of 3% sucrose, half-strength Gamborg's B5 salts and full-strength Gamborg's vitamins with the pH adjusted to 5.7. The 50-ml cultures were grown in 250-ml Erlenmeyer flasks to late exponential phase in the dark at 26° C. at 100 rpm.

Extraction of hairy roots: The powdered hairy roots of *C. roseus* (200 g) were immersed in methanol (1.5 liter) for three days at room temperature and then the supernatant was concentrated under vacuum to yield 22.5 g of the extract. This material was suspended in water and extracted with ethyl acetate and n-butanol successively to produce 11.2 g of ethyl acetate and 7.4 g of n-butanol extract.

Isolation of the compounds from ethyl acetate extract: The entire ethyl acetate extract was subjected to normal phase column chromatography over silica gel (400 g) to yield 26 fractions (each fraction 250 mL) with the following eluants: fractions 1-2 with n-hexane, fractions 3-4 with n-hexane: ethyl acetate (9:1, v/v), fractions 5-6 with n-hexane:ethyl acetate (8:2, v/v), fractions 7-8 with n-hexane:ethyl acetate (7:3, v/v), fractions 9-10 with n-hexane:ethyl acetate (1:1, v/v), fractions 11-12 with hexane:ethyl acetate (3:7, v/v), fractions 13-14 with ethyl acetate, fractions 15-16 with ethyl acetate:methanol (9.5:0.5, v/v), fractions 17-18 with ethyl acetate:methanol (9:1, v/v), fractions 19-20 with ethyl acetate:methanol (7:3, v/v), fractions 21-22 with ethyl acetate:methanol (1:1, v/v), fractions 23-24 with ethyl acetate:methanol (3:7, v/v), and fractions 25-26 in methanol. All the fractions were examined by TLC and compounds (1-16) isolated and purified from above fractions by normal and reverse phase chromatography.

Thin layer chromatography analyses were performed on precoated silica gel 60 $F_{254}$ plates (MERCK®) and visualization of plates was performed using a 5% $H_2SO_4$ in $C_2H_5OH$ spray reagent. Column chromatography was performed using silica gel (70-230 mesh) and LICHROPREP RP-18™ (40-63 µm; ODS silica gel) from MERCK®.

Instrumentation: Melting points were determined using ELECTROCHEMICAL ENGINEERING™ model IA9100 melting point apparatus (ELECTROTHERMAL®, Seoul, South Korea). Specific rotation was measured with an INSTRUMENTS LTD™ model AA-10 polarimeter (Seoul, South Korea). $^1H$- and $^{13}C$-NMR spectra were obtained at 500 and 125 MHz, respectively, using a BRUKER AVANCE™ model DRX-500 spectrometer at the Seoul National University (SNU), Seoul, South Korea. NMR spectra were obtained in deuterated chloroform and methanol using TMS as an internal standard, with chemical shifts expressed in ppm (δ) and coupling constants (J) in Hz. EIMS and FABMS were recorded on JEOL™ JMS-SX 102A and JEOL™ JMS-AX 505WA spectrophotometers (Japan Electron Optics Laboratory, Tokyo, Japan), respectively, at the Seoul National University. IR spectra were recorded on a THERMO MATTSON INFINITY GOLD™ FT-IR model 60-AR spectrophotometer at the Korea Institute of Science and Technology (KIST) Seoul, South Korea.

EXAMPLE 1

FLAVONOID GLYCOSIDE COMPOUNDS

Four new flavonoid glycoside compounds (1), (2), (3), and (4), along with the three known compounds were isolated from the methanol extract of *C. roseus* hairy roots. The isolation and structural elucidation of these new flavonoid glycoside compounds was achieved through spectral analysis by means of $^1H$ and $^{13}C$ NMR, and DEPT, including 2D-NMR COSY, HETCOR, HSQC and chemical reactions (U.S. Ser. No. 60/890,482 filed Feb. 18, 2007; U.S. Ser. No. 60/977,647 filed Oct. 4, 2007 all incorporated herein by reference in their entirety). THP-1 cells activated with LPS were treated with these new flavonoid glycosides. The glycosides inhibited both MMP-9 activity and TNF-α production in these cells.

Fractions 17-18 with ethyl acetate:methanol (9:1) of the first column were and chromatographed with $CHCl_3$:methanol (99:1, 97:3, 95:5, 93:7 and 9:1) and separated into five fractions (frs. 1 to frs. 5). Fractions 3-5 were mixed and re-chromatographed over a LICHROPREP™ RP-18 (ODS silica gel; 40-63 µm; 50 g; each fraction 50 mL). The compounds were eluted sequentially with methanol containing 80, 60, 40, 20, 10 and 0% water to yield four compounds (1) (18 mg), (2) (19 mg), (3) (21 mg) and (4) (23 mg).

The four new flavonoids glycoside compounds 3,5,7-trihydroxy-3',4'-dimethoxyflavone-7β-D-glucopyranosyl(4"-13'")2'",6'",10'",14'"-tetramethyl hexadec-14-ene (1), 3,5,7-trihydroxy-4'-methoxyflavone-3β-D-glucopyranosyl(4"-13'")-2'",6'",10'",14'"-tetramethyl hexadecane (2), 6"-(3',11'"-dimethyl dodec-3'",7'"(14'"), 10'"-trienyl glucopyranosyl-7-hydroxy-3',4'-dimethoxyflavanone (3) and 6"-(3'",11'"-dimethyl-7'"-hydroxymethylene dodecanyl) glucopyranosyl-7,3'-dihydroxy-4'-methoxyflavanone (4) along with the three known compounds (13), (14), and (16) were isolated from the methanolic extract of *C. roseus* hairy roots. Their structures were elucidated with the help of different spectroscopic techniques.

Compound (1), was obtained as a pale yellow crystalline mass from (ethyl acetate:methanol; 9:1) eluants. It responded to positive tests of flavonoid glycosides. Its IR spectrum showed characteristic absorption bands suggested that a phytol-like moiety was attached at the terminal position of the molecule and a glucose moiety was linked to the flavone nucleus and two methoxy groups were attached in ring B. The $^1H$ NMR spectrum of (1) showed important signals for flavone carbonyl carbon. Acid hydrolysis of (1) yielded D-glucose (TLC comparable). On the basis of spectral data analysis and chemical reactions the structure of (1) has been established as 3,5,7-trihydroxy-3',4'-dimethoxyflavone-7β-D-glucopyranosyl (4"-13'")-2'",10'",14'"-tetramethyl hexadec-14-ene.

Compound (2), was obtained as a pale yellow crystalline mass from (ethyl acetate:methanol; 9:1) eluants. It responded to positive tests of flavonoid glycoside. Its IR spectrum showed characteristic absorption bands for hydroxyl groups and conjugated carbonyl group and suggested a saturated phytol-type moiety was attached to the flavone glycoside. The $^1H$ NMR spectrum of (2) displayed characteristics of flavone and glucopyranosides. Acid hydrolysis of (2) yielded D-glucose (TLC comparable). On the basis of spectral data analysis and chemical reactions, the structure of (2) has been formulated as 3,5,7-trihydroxy-4'-methoxyflavone-3β-D-glucopyranosyl (4"-13'")-2'",6'",10'",14'"-tetramethyl hexadecane.

Compound (3), was obtained as a pale yellow crystalline mass from (ethyl acetate:methanol; 9:1) eluants. It responded to positive tests of flavonoid glycosides. Its IR spectrum showed characteristic absorption suggested that a flavanone was an aglycone moiety possessing one hydroxyl group in ring A and two methoxy groups in ring B. Further analysis indicated that (3) was an acyclic sesquiterpenic acid possessing three vinylic linkages at carbons C3", C7" (14") and C-10" was esterified with the sugar moiety. The 1H NMR spectrum of (3) exhibited the presence of aromatic carbons and sugar carbons. Acid hydrolysis of (3) yielded β-D-glucose as a glycone moiety (TLC comparable). On the basis spectral data analysis of (3), the structure has been established as 6"-(3'",11'"-dimethyl-dodec-3'",7'"(14'") 10'"-trienyl glucopyranosyl-7-hydroxy-3',4'-dimethoxyflavanone.

Compound (4), was obtained as a pale yellow crystalline mass from (ethyl acetate:methanol; 9:1) eluants. It also reacted positively to flavonoid glycoside assays. The IR spectrum showed characteristic absorption bands corresponding to the molecular formula of a flavanone glycoside attached with an acyclic sesquiterpenoid. A complete molecular formula ($C_{37}H_{52}O_{12}$) was obtained from HR-FAB/MS. Ion analysis indicated the presence of one hydroxyl group in ring A and one each hydroxyl and methoxyl groups in ring B of flavanone moiety. Acid hydrolysis of (4) yielded β-D-glucose as a glycone moiety (TLC comparable). On the basis of spectral data analysis and chemical reactions, the structure of new compound has been elucidated as 6"-(3'", 11'"-dimethyl-7'"-hydroxymethylene dodecanyl) glucopyranosyl-7,3'-dihydroxy-4'-methoxyflavanone.

The known compounds, (16) (Chung, 2005), (13) (Mahato et al., 1994; Kitjima et al., 1990), and (14) were identified by comparing current results with those reported earlier. However this is the first report of isolating the two compounds, (13) and (14), from this particular plant.

EXAMPLE 2

N-HEPTACOSAN-13-ALPHA-OL-13BETA-D-GLUCOPYRANOSIDE

A new long chain aliphatic glycoside (5) along with known compounds, (15) and (16) were isolated from the methanolic extract of the cultured hairy roots of C. roseus. The structures of these compounds were elucidated by a combination of spectral methods including IR, EIMS, FABMS, $^1$H and $^{13}$C NMR (Ahmad, 2008; U.S. Ser. No. 60/890,482 filed Feb. 18, 2007 both incorporated herein by reference in their entirety). To the best of our knowledge, n-hentetracont-36-en-5β-ol was identified for the first time from the hairy roots of C. roseus.

Compound (5) was obtained as a colorless crystalline mass and yielded a positive result in a glycoside assay. On the basis of spectral data analysis and chemical reactions the structure of (5) has been elucidated as n-heptacosan-13α-ol-13β-D-glucopyranoside, see Table 2.

Compound (15) was obtained as a colorless product and it decolorized bromine water indicating unsaturated nature of the molecule. Its IR spectrum showed characteristic absorption bands for hydroxyl group (3435 cm$^{-1}$), unsaturation (1634 cm$^{-1}$) and long aliphatic chain (722 cm$^{-1}$). On the basis of spectral analyses the structure of (15) has been established as n-hentetracont-36-en-5β-ol.

EXAMPLE 3

3,7,11,19,23,27-HEXAMETHYL-15-HYDROXYM-ETHYLENE-N-OCTACOS-5,8,20-TRIENE-10BETA, 18-ALPHA-DIOL-10BETA-D-GLU-COPYRANOSIDE

One new compound (6) along with the three known compounds (13), (14) and (16) were isolated from the methanolic extract of the cultured C. roseus hairy roots. The structures of the one new and three known compounds were elucidated using one- and two-dimensional NMR in combination with IR, EI/MS, FAB/MS (Chung, 2007a; U.S. Ser. No. 60/890, 482 filed Feb. 18, 2007 both incorporated herein by reference in their entirety). To the best of our knowledge this is the first purification of 3,7,11,19,23,27-hexamethyl-15-hydroxymethylene-n-octacos-5,8,20-triene-10β, 18α-diol-10β-D-glucopyranoside, 3-epibetulinic acid (13) and n-pentadecanyl octa-dec-19-en-oate (14) from C. roseus hairy roots.

The hexane:ethyl acetate fractions 7-8 (0.6 g) were further purified by column chromatography over silica gel (100 g; each fraction of 100 mL) eluting with dichloromethane and chloroform:methanol mixtures (99:1, 98.5:1.5, 98.2, 97.5:2.5 and 97:3, v/v) to afford one pure compound (120 mg, (12)). Fractions 11-12 with hexane:ethyl acetate (3:7, v/v), after re-separation with chloroform:methanol (99:1, 99:2, 97:3, 96:4 and 95:5, v/v), afforded five fractions. Fraction 4 (from the eluent of CHCl$_3$:MeOH (96:4, v/v)) and fraction 5 (from the eluent of chloroform:methanol (95:5, v/v)) were re-chromatographed over LiChroprep™ RP18 ODS (50 g; each fraction of 50 mL). The eluting was sequentially performed with methanol containing 80, 60, 40 20, 10, and 0% of water to yield compounds (6) (35 mg) and (13) (23 mg).

Compound (6) was obtained as a light yellow semisolid crystalline mass. It responded positive tests for glycosides. Its IR spectrum showed characteristic absorption bands for hydroxyl groups (3420, 3390, 3285 cm-1), ester group (1736 cm-1), and unsaturation (1640 cm$^{-1}$). The multiplicity of each carbon was determined by DEPT experiments. There were nine primary, thirteen methylene, twenty methine, and one quaternary carbon in the molecule. The HMBC shows the correlation between the anomeric proton of the glucose and C-10. This indicates that the sugar moiety is attached to C-10. Also, H-32 and methyl protons in the O-acetyl group showed the correlation with the carbonyl carbon. On the basis of detailed spectral analyses the structure of (6) has been established as 3,7,11,19,23,27-hexamethyl-15-hydroxymethylene-n-octacos-5,8,20-triene-10,18-diol-10-β-D-glucopyranoside. This is a new compound isolated from the cultured hairy roots of C. roseus.

Compound (13) was obtained as a colorless crystalline mass from the chloroform:methanol (95:5) eluent system. It responded positively to Liebermann-Burchard test for triterpenes. On the basis of spectral data analysis and chemical reactions, the structure of (13) has elucidated as lup-20(29)-en-18-βH-3α-ol which is a previously reported compound (Sansei, et al., 1996).

Compound (14), an aliphatic ester, was obtained as a yellow gum mass from the eluent system of chloroform:methanol (95:5). It decolorized bromine water which indicates the presence of unsaturated linkage(s) in the molecule. Its IR spectrum suggested that an oleic acid group is esterified with a 15 C aliphatic moiety. The $^1$H-NMR spectrum of (14) further confirmed the structure as n-pentadecanyl octa-dec-19-en-oate and acid hydrolysis of (14) yielded oleic acid which was confirmed by co-TLC with an authentic sample of oleic acid. On the basis of spectral data analysis and chemical reactions, the structure of (14) has been established as n-pentadecanyl octa-dec-19-en-oate.

EXAMPLE 4

ANTHRACENES

Two new compounds (7) and (8) have been isolated from the hairy root cultures of C. roseus. Their structures have been elucidated through 500 MHz NMR techniques using one- and two-dimensional NMR in combination with IR, EI/MS, FAB/MS and HR-FAB/MS spectroscopy (Chung, 2007b; U.S. Ser. No. 60/890,482 filed Feb. 18, 2007 both incorporated herein by reference in their entirety). To the best of our knowledge this is the first purification of these novel anthracene molecules.

The first compound (7) was obtained as a dark yellow crystalline mass and its molecular formula ($C_{52}H_{70}O_{10}$) was deduced from HR-FAB/MS. It tested positive for triterpenic glycosides and produced effervescences with sodium bicarbonate indicating the presence of carboxylic acid in the molecule. The structure of (7) has been established as lanast-5,8-dien-3β-ol-27-oic acid-3β-D-glucopyranosyl (4'-1")-10", 11"-dimethoxy anthracene. This is a new lanastenenol glycoside isolated for the first time.

Compound (8) was obtained as a dark yellow crystalline mass from ethyl acetate:methanol; 9.5:0.5) eluants. It responded positively to glycosidic tests. On the basis of detailed structural analyses, the structure of 8 has been established as 2-methoxy-6-(n-nonacontan-5",6"-dionyl)-11-hydroxy-13-methyl-11β-D-rhamnopyranoside anthracene. This is new anthracene derivative isolated for the first time.

EXAMPLE 5

CATHARANTHUSOPIMARANOSIDES

Two new compounds (9) and (10) have been isolated from the hairy root cultures of C. roseus. Their structures were elucidated with the help of 500 MHz NMR using 1D and 2D spectral methods viz: NMR, $^1$H-$^1$H COSY, $^1$H-$^{13}$C HETCOR etc., and DEPT aided by EIMS, FABMS and IR spectroscopy. (Chung, 2008a; U.S. Ser. No. 60/890,482 filed Feb. 18, 2007 both incorporated herein by reference in their entirety). On the basis of spectral data analysis and chemical reaction the structure of catharanthusopimaranoside A (9) has been established as 3-methoxy-6,8-dimethyl-β-naphthyl-β-D-glucopyranosyl-6'-pimaran-17"-oic acid ester. This is an unreported naphthalene glucoside. The structure of catharanthusopimaranoside B (10) has been formulated as 1-methoxy-7,8-dimethyl-β-naphthyl-β-L-arabinopyranosyl-4'-pimaran-17"-oic acid ester. These are new diterpene glycosides isolated from C. roseus roots.

EXAMPLE 6

SESQUITERPENE GLYCOSIDES

Two new compounds guaia-1,7-dien-3β, 13-diol-13α-D-glucofuranoside (11) and cadin-2-en-1β-ol-1β-D-glucuronopyranoside (12), along with three known compounds have been isolated from the cultures hairy root of C. roseus. Their structures were elucidated through 500/125 MHz NMR using 1D and 2D spectral methods: viz: $^1$H and $^{13}$C NMR, $^1$H-$^1$H COSY, $^1$H-$^{13}$C HETCOR etc., and DEPT aided by EIMS, FAB-MS, HR-FABMS and IR spectroscopy. (Chung, 2008b; U.S. Ser. No. 60/890,482 filed Feb. 18, 2007, both incorporated herein by reference in their entirety). These new sesquiterpene glycoside compounds were isolated for the first time.

Compound (11) was obtained as a colorless crystalline mass from ethyl acetate:methanol (9.5:0.5) eluants and its molecular formula was deduced as $C_{21}H_{34}O_7$ from its $^{13}$C NMR and HR-FABMS. On the basis of spectral data analysis and chemical reactions the structure of (11) was established as guaia-1,7-dien-3β, 13-diol-13α-D-glucofuranoside. This is a new sesquiterpene glycoside.

Compound (12) was obtained as a colourless crystalline mass from ethyl acetate:methanol (9.5:0.5) eluent and its molecular formula was deduced as $C_{21}H_{34}O_7$ from its $^{13}$C NMR and HR-FABMS. It gave effervescence with sodium bicarbonate solution and gave positive results for glycoside assays. On the basis of the spectral data analyses and chemical reactions the structure of (12) was established as cadin-2-en-1β-ol-1β-D-glucuronopyranoside. This is a new phytoconstituent isolated for the first time.

EXAMPLE 7

PHARMACEUTICAL ACTIVITY

Several of the compounds were tested for pharmaceutical activity against two well known inflammatory mediators—MMP-9 and TNF-α. Compounds (1), (2), (3), and (4), were tested. An inflammatory reaction is stimulated with LPS and MMP-2 is used as an internal gene expression control.

The inhibitory effect of flavonoid glycoside compounds on MMP-9 expression (FIG. 1) was assayed in THP-1 cells stimulated with LPS. In panels A, C, E and G; THP-1 cells were pre-treated with 5, 10 and 20 µg/ml of the compound specified for 2 h. After pre-treatment with the relevant compound, the cells were then stimulated with 1 µg/ml LPS. The culture supernatants were collected 24 h after activation and subjected to substrate gel electrophoresis (gelatin zymography) and staining with Coomassie brilliant blue.

In panels B, D, F and H; THP-1 cells were treated with the compound in A, C, E and G, and cell viability was tested with MTS assay. This demonstrates that the MMP-9 was inhibited without reducing cell viability, and suggests the use of the compounds in treating MMP-9 mediated inflammatory responses. Also, treatment of cancer cells such as A549, CaSki, DLD-2, and MCF-7 cells with these new flavonoid glycosides revealed that they were not cytotoxic (data not shown). These data indicate that compounds purified from the C. roseus are not cytotoxic.

Figure 2:
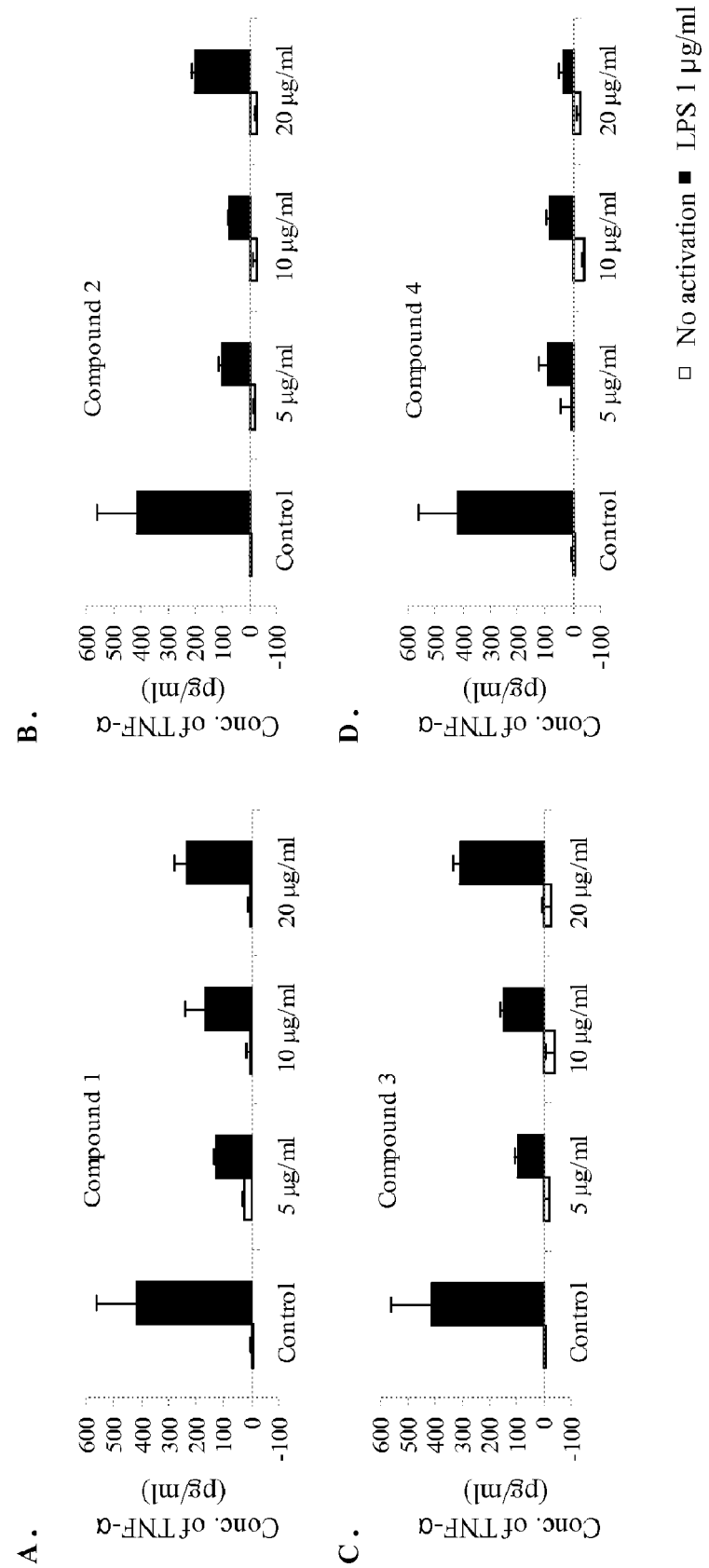
FIGS. 2A-D shows compounds (1), (2), (3), and (4) and their effect on TNF-α levels with and without stimulation of inflammation by LPS.

The blocking effect of compounds on cytokines expression (FIG. 2) induced by LPS in monocytic cell lines was then assessed. THP-1 cells were pre-treated with compounds for 2 h and activated with 1 µg/ml LPS. Culture supernatants were collected in 24 h and the TNF-α concentrations were measured using sandwich ELISA. Measurements were done in duplicate. The four compounds blocked cytokine expression of pro-inflammatory cytokines, such as TNF-α. Therefore the compounds work to suppress inflammatory response and are potent anti-inflammatory compounds.

This study was focused on the anti-inflammatory effect of the four new flavonoid glycoside compounds (1), (2), (3), and (4). These flavonoids inhibited both MMP-9 activity (FIG. 1) and TNF-α production (FIG. 2) in THP-1 cells treated with LPS, without affecting cell viability. Therefore, these four new flavonoid glycoside compounds can be regarded as promising drug candidates for the treatment of inflammatory diseases.

EXAMPLE 9

LARGE SCALE PRODUCTION WITH HAIRY ROOT CULTURES

Hairy roots provide a unique opportunity to produce cellular compounds in a culture environment. Unlike individual cell cultures, hairy roots behave similar to leaves and roots of the adult plant. But, unlike the adult plant, growth of hairy roots in culture is not limited.

Hairy roots are generated and grown in small cultures, as previously described. The small cultures are used to inoculate fermentors, bioreactors or other large capacity cell culture apparatus. The cultures are grown to density and the hairy root mass isolated. The hairy root mass can then be used for the large scale (gram to kilogram scale) production of chemical compounds. These compounds are superior to chemically synthesized compounds because they do not require expensive reagents and starting compounds, they can be produced without a lot of waste, and multiple compounds can be produced and isolated simultaneously.

The isolated novel compounds described herein will provide useful pharmaceuticals for the treatment of inflammatory conditions.

All references are listed herein for the convenience of the reader. Each is incorporated by reference in its entirety.
1. AHMAD and CHUNG. A New Aliphatic Glycoside Constituent from the Hairy Root Cultures of C. roseus. Asian Journal of Chemistry. 20: 642-8 (2008).
2. Bhadra, et al., "Production of indole alkaloids by hairy root lines of C. roseus." Biotechnol. Bioeng., 41:581-92 (1993).
3. Chockalingam, et al., "Impact of the extract of C. roseus on feeding and enzymatic digestive activities of Spodoptera litura." J. Environ. Biol. 10:303-7 (1989).

4. CHUNG, et al., "A new chemical constituent from the hairy root cultures of *C. roseus*." Bull. Korean Chem. Soc. 28:229-34 (2007a).
5. CHUNG, et al., Identification of new compounds from *C. roseus* hairy root cultures. Bull. Korean Chem. Soc. 28: 1294-8 (2007b).
6. CHUNG, et al., "New Sesquiterpene Glycosides from Cultures Hairy Roots of *C. roseus*." Chin. J. Chem. 25: 1695-99 (2007c).
7. CHUNG, et al., "New *Catharanthusopimaranoside* A and B from Culture Hairy Roots of *C. roseus*." Chemistry of Natural Compounds (2008a) [Accepted].
8. CHUNG, et al., "New Flavonoid Glycoside Identification from the Hairy Roots of *C. roseus* and Their Anti-inflammatory Effect. Phytochemistry, (2008b) [submitted, under review].
9. Daniel and Sabnis, "Chemotaxonomical studies on *Apocynaceae*." Indian J. Exp. Biology, 16:512-8 (1978).
10. Farnsworth, N. R. "The pharmacology of the Periwincles: *Vinca* and *Catharanthus*." Lloydia (J. Nat. Prods.), 24:105-37 (1961).
11. Gilles et al., A new flavonol glycoside from *Catharanthus roseus*. Phytochemistry 50:167-9 (1999).
12. Kitajima, et al., "Two new triterpenoid sulfates from the leaves of Schefflera octophylla." Chem. Pharm. Bull. 38:714-6 (1990).
13. Knobloch, et al., "Medium and light induced formation of serpentine and anthocyanins in cell suspension cultures of *C. roseus*." Phytochemistry 21:591-4 (1982).
14. Leveque, et al., "Pharmacology of *Catharanthus* alkaloids." Bull. Cancer 83:176-86 (1996).
15. Luijendijk, et al., "Involvement of strictosidine as a defensive chemical in *C. roseus*." J. Chemical Ecology 22:1355-66 (1996).
16. Moreno, et al., "Cell and tissue cultures of *C. roseus* (L.) G. Don: A literature survey II. Updating from 1988 to 1993". Plant Cell Tiss. Org. Cult 42:1-25 (1995).
17. Moreno, et al., "Effects of elicitation on different metabolic pathways in *C. roseus* (L.) G. Don cell suspension cultures." Enzyme and Microbial Technology, 18:99-107 (1996).
18. Nippon Kouteisho Kyokai, "Japanese Pharmacopeia XII," Hirokawa Tokyo, pp. C2341-C2553 (1991).
19. Nishibe, et al., "Bioactive Phenolic Compounds from *C. roseus* and *Vinca* minor." Natural Medicine (Tokyo) 50:378-84 (1996).
20. Sansei, et al., "Bioactive phenolic compounds from *C. roseus* and *Vinca* minor." Natural Medicines 50:378-83 (1996).
21. Seitz, et al., "Elicitor-mediated induction of phenylalanine ammonia lyase and tryptophan decarboxylase: Accumulation of phenols and indole alkaloids in cell suspension cultures of *C. roseus*." Plant Cell Tiss. Org. Cult. 18:71-8 (1989).
22. Taylor and Farnsworth, "The *Catharanthus* Alkaloids." New York: Marcel Dekker (1975).
23. van Der Heijden, et al., "Cell and tissue cultures of *C. roseus* (L.) G. Don: A literature survey." Plant Cell Tiss. Org. Cult. 18:231-80 (1989).

What is claimed is:
1. An isolated and purified chemical compound selected from the group consisting of:

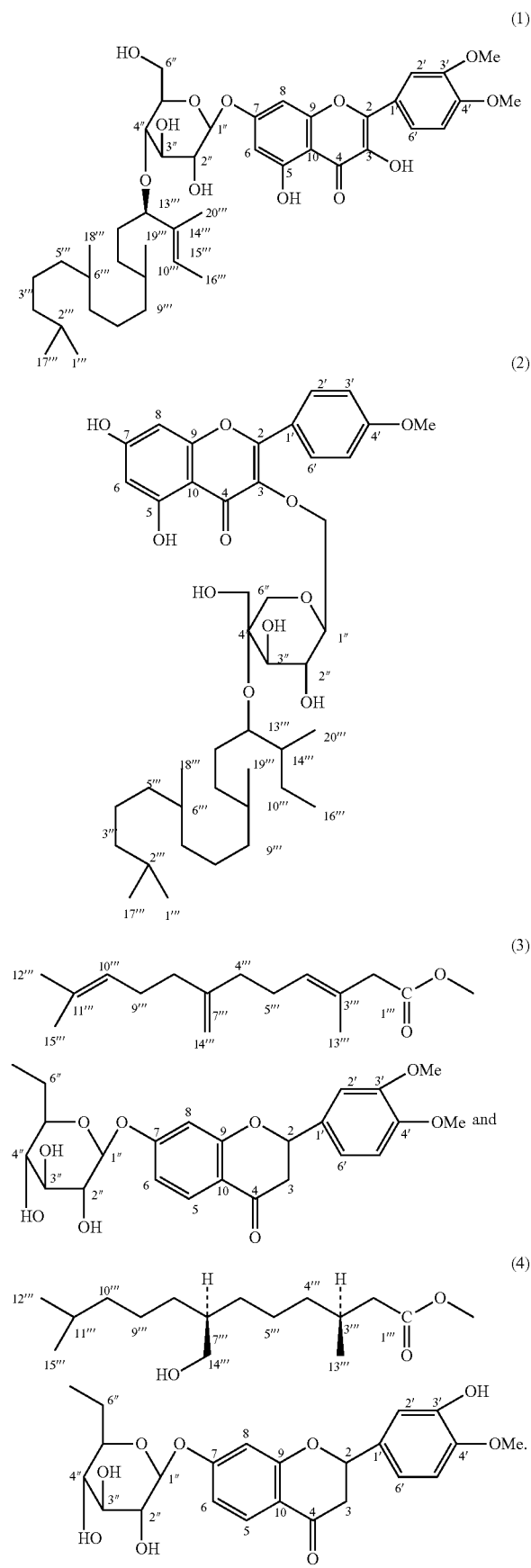

2. A composition comprising an isolated and purified flavone glycoside selected from the group consisting of formula:
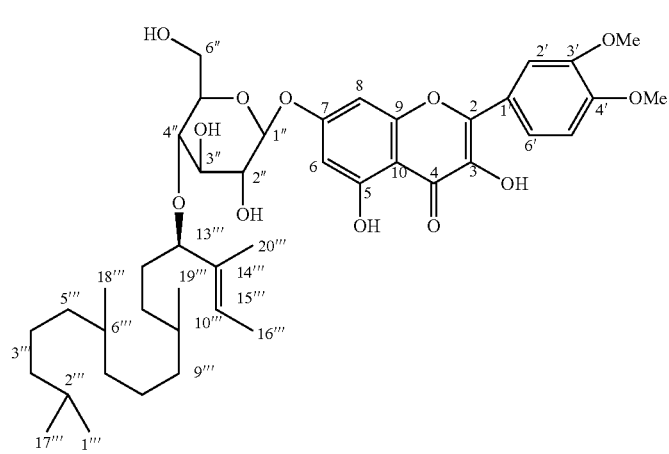
(1)
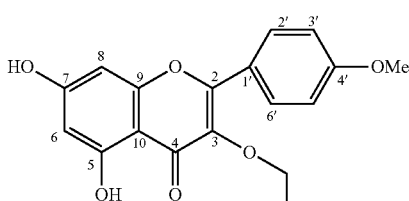
(2)
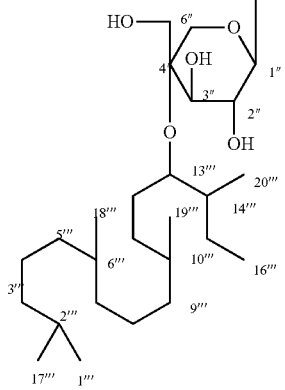
(3)
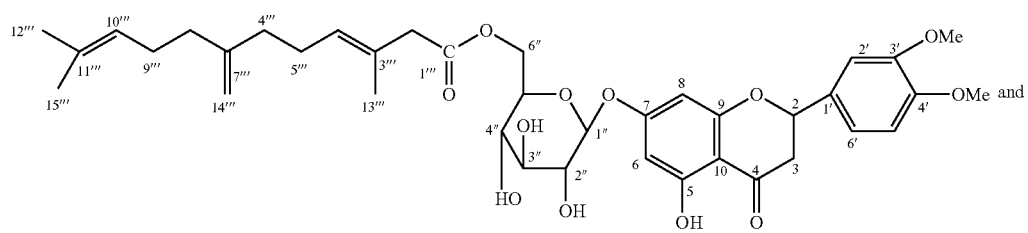
and
(4)
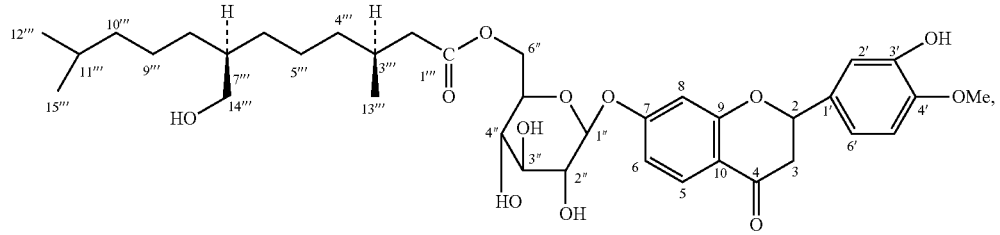
together with a pharmaceutically acceptable carrier.

3. The composition of claim 2, where the flavone glycoside is at least 90% pure before admixture with the pharmaceutically acceptable carrier.

4. The composition of claim 2, where the flavone glycoside is at least 95% pure before admixture with the pharmaceutically acceptable carrier.

5. The composition of claim 2, wherein the flavone glycoside is formula (1).

6. The composition of claim 2, wherein the flavone glycoside is formula (2).

7. The composition of claim 2, wherein the flavone glycoside is formula (3).

8. The composition of claim 2, wherein the flavone glycoside is formula (4).

* * * * *